United States Patent [19]
Brunie et al.

[11] 3,947,490
[45] Mar. 30, 1976

[54] PROCESS FOR PREPARING OMEGA-FORMYLOXY-ALKANALS

[75] Inventors: Jean Claude Brunie, Francheville-le-Haut; Michel Costantini; Noël Crenne, both of Lyon; Michel Jouffret, Francheville-le-Bas, all of France

[73] Assignee: Rhone-Poulenc S.A., Paris, France

[22] Filed: May 31, 1974

[21] Appl. No.: 475,041

[30] Foreign Application Priority Data
June 4, 1973 France .............................. 73.20228

[52] U.S. Cl. ...... 260/488 F; 260/488 R; 260/530 R; 260/586 R; 260/635 R
[51] Int. Cl.² ......................................... C07C 67/00

[58] Field of Search .................................. 260/488 F

[56] References Cited
UNITED STATES PATENTS

| | | | |
|---|---|---|---|
| 3,689,534 | 9/1972 | Brunie et al. ..................... | 260/488 F |
| 3,784,567 | 1/1974 | Isard et al ....................... | 260/488 F |

*Primary Examiner*—Vivian Garner
*Attorney, Agent, or Firm*—Stevens, Davis, Miller & Mosher

[57] ABSTRACT

An improved process for preparing ω-formyloxy-alkanals from the corresponding cycloalkyl peroxides and formic acid is provided in which the process is carried out in the presence of a small amount of a strong acid having a pKa of less than 2.

9 Claims, No Drawings

PROCESS FOR PREPARING OMEGA-FORMYLOXY-ALKANALS

This invention relates to a process for preparing ω-formyloxy-alkanals.

U.S. Pat. No. 3,689,534 describes ω-formyloxy-alkanals of the general formula:

$$HC(O)O(CH_2)_nCHO \qquad (I)$$

in which the symbol $n$ represents an integer from 5 to 11.

A process for the preparation of these compounds is also described; this process consists of reacting formic acid with a cycloalkyl hydroperoxide of the formula:

in which $n$ is as defined above.

The hydroperoxides of formula (II) can be prepared from the corresponding cycloalkanols, or from the corresponding cycloalkanes by oxidation, in the liquid phase, without a catalyst, by a gas containing molecular oxygen. For example, it is possible to oxidise cyclohexane in accordance with the process described in French Pat. No. 1,404,723, or a higher homologue in accordance with the process described in French Pat. No. 1,429,569, and then to purify the hydroperoxide formed by conventional processes, such as conversion to the sodium salt and treatment with carbon dioxide.

U.S. Pat. No. 3,689,534 indicates that a practical way of carrying out this process consists of introducing pure hydroperoxide gradually into formic acid which does not contain more than 5% by weight of water and which has been heated beforehand to from 50°C to the boiling point.

The amount of formic acid employed is not critical since it can be used as a diluent, and is generally used in an amount in excess of 5 mols per mol of hydroperoxide.

When the introduction of the hydroperoxide is complete, it is recommended to remove from the reaction mixture the formic acid which has not taken part in the reaction, because its presence can have a detrimental effect on the stability of the formyloxy-alkanal formed; one method for achieving this result is azeotropic distillation.

The formyloxy-alkanal formed can then be isolated from the residual mixture in accordance with conventional methods, for example by fractional distillation, preferably under reduced pressure. The yields obtained are, however, restricted by various side reactions, for example that leading to cycloalkanones and cycloalkyl formates, these being isolated in addition to the desired formyloxy-alkanal.

ω-Formyloxy-alkanals are very valuable intermediates. They can, for example, be converted to α, ω-alkane-diols or to ω-hydroxy-alkanoic acids which are valuable precursors for producing resins and synthetic fibres. In order to increase the value of this process, it is thus very desirable to minimize the formation of unwanted by-products to a greater extent and it is the object of the present invention to achieve this.

According to the present invention, the splitting reaction involving formic acid is carried out in the presence of a small amount of an anhydrous strong acid having a pKa of less than 2.

In order to carry out the process according to the present invention, inorganic or sulphonic acids possessing a pK of less than 2 are used. The following acids are especially suitable: hydrochloric acid, nitric acid, sulphuric acid, alkane-sulphonic acids such as methane-sulphonic acid, and arylsulphonic acids such as benzene-sulphonic acid and para-toluene-sulphonic acid.

The general conditions for carrying out the process are substantially the same as those described in the U.S. Specification referred to above, to which reference should be made for further details. The cycloalkyl hydroperoxide is suitably introduced pure into formic acid containing the desired amount of strong acid, heated beforehand to the chosen temperature. The amount of strong acid to be used is suitably from 0.005 to 0.5 hydrogen ion per liter of formic acid introduced, and preferably from 0.01 to 0.2 hydrogen ion per liter of formic acid.

Where appropriate, the cycloalkyl hydroperoxide starting material can be used in dilute form, for example in the form of a solution in a suitable aprotic polar solvent such as sulpholane, ethylene glycol carbonate or propylene glycol carbonate. The solution of hydroperoxide employed is advantageously the solution resulting from the extraction of the cycloalkyl hydroperoxide from the crude oxidised products of the hydrocarbon from which it is derived, using such polar solvents.

The splitting reaction can also be effected by introducing, at the desired temperature, pure hydroperoxide into a mixture of formic acid and the strong acid dissolved in the selected solvent.

When the introduction of the hydroperoxide is complete, the reaction is generally allowed to continue for a few moments at the desired temperature and then the strong acidity is neutralised with a large excess of a salt of a weak acid and a strong base, for example sodium formate. The reaction mixture resulting from the splitting process can then be treated in different ways. For example, the ω-formyloxy-alkanal formed can be isolated, but it is also possible to treat the reaction mixture directly so as to convert these difunctional compounds, in situ, to industrially valuable products such as α,ω-alkanediols and ω-hydroxy-alkanoic acids.

The following Examples further illustrate the present invention.

EXAMPLES 1 to 3

Formic acid, the water content of which is 0.5% by weight, and to which methane-sulphonic acid has been added, is heated to the desired temperature in a flask equipped with a stirring system. 97% By weight pure cyclohexyl hydroperoxide is then added as rapidly as possible (in 30 to 60 seconds) to the mixture. When the addition is complete, the reaction is allowed to continue for a short while, and then the sulphonic acid is neutralised with a 100% excess of sodium formate, and cooled by means of an external cold water bath. The products of the reaction, i.e. the yields of 6-formyloxy-hexanal, cyclohexanone and cyclohexyl formate, relative to the pure cyclohexyl hydroperoxide introduced, is determined by vapour phase chromatographic analyses.

Three experiments are carried out with increasing concentrations of methane-sulphonic acid in formic acid, namely 0.016 mol per liter (Example 1), 0.032 mol per liter (Example 2) and 0.16 mol per liter (Example 3).

The results are given in the following table:

| Example | 1 | 2 | 3 |
|---|---|---|---|
| Pure formic acid, mol | 0.865 | 0.865 | 0.865 |
| Pure cyclohexyl hydroperoxide, mol | 0.02 | 0.02 | 0.02 |
| Concentration of methane-sulphonic acid in formic, acid, in mol/l. | 0.016 | 0.032 | 0.16 |
| Molar ratio: Formic acid / Hydroperoxide | 43 | 43 | 43 |
| Temperature, °C | 100 | 100 | 100 |
| Duration in minutes | 2 | 2 | 2 |
| Yield of 6-formyloxy-hexanal | 51.3% | 66.5% | 38% |
| Yield of cyclohexanone | 22% | 21% | 15.6% |
| Yield of cyclohexyl formate | 4.4% | 3.8% | 5.2% |
| Total yield | 77.7% | 91.3% | 58.8% |

We claim:

1. In a process for the preparation of an ω-formyloxy-alkanal of the general formula:

$$HC(O)O(CH_2)_nCHO$$

in which $n$ represents an integer from 5 to 11, which comprises reacting formic acid with a cycloalkyl hydroperoxide of the formula:

in which $n$ is as defined above, the improvement wherein the reaction is carried out in the presence of 0.005 to .5 hydrogen ion per liter of formic acid of a strong acid with a pK of less than 2.

2. Process according to claim 1, in which the strong acid is an inorganic or sulphonic acid.

3. Process according to claim 2, in which the strong acid is selected from hydrochloric acid, nitric acid and sulphuric acid.

4. Process according to claim 2, in which the strong acid is selected from methane-sulphonic acid, benzene-sulphonic acid and para-toluene-sulphonic acid.

5. Process according to claim 1, in which the strong acid is present in an amount from 0.01 to 0.2 hydrogen ion per liter of formic acid introduced.

6. Process according to claim 1, which is carried out in the liquid phase at a temperature from 50°C to the boiling point of the reaction mixture.

7. Process according to claim 1, in which the formic acid is used in an amount greater than 5 mols per mol of hydroperoxide.

8. Process according to claim 1, in which the cycloalkyl hydroperoxide is present as a solution in an aprotic polar solvent.

9. Process for the preparation of ω-formyloxyhexanal which comprises reacting cyclohexyl hydroperoxide with formic acid in the presence of 0.005 to 0.5 hydrogen ion per liter of formic acid of a strong acid having a pKa of less than 2.

* * * * *